(12) United States Patent
Sarzaeem

(10) Patent No.: US 11,766,269 B2
(45) Date of Patent: Sep. 26, 2023

(54) DISTAL FEMORAL CUTTING BLOCK INSTRUMENT

(71) Applicant: Mohammad Mahdi Sarzaeem, Tehran (IR)

(72) Inventor: Mohammad Mahdi Sarzaeem, Tehran (IR)

(*) Notice: Subject to any disclaimer, the term of this patent is extended or adjusted under 35 U.S.C. 154(b) by 0 days.

(21) Appl. No.: 18/089,235

(22) Filed: Dec. 27, 2022

(65) Prior Publication Data

US 2023/0130250 A1  Apr. 27, 2023

Related U.S. Application Data

(63) Continuation of application No. 17/956,468, filed on Sep. 29, 2022.

(51) Int. Cl.
*A61B 17/17* (2006.01)
*A61B 17/15* (2006.01)
*A61B 17/56* (2006.01)

(52) U.S. Cl.
CPC ........ *A61B 17/1764* (2013.01); *A61B 17/155* (2013.01); *A61B 2017/564* (2013.01)

(58) Field of Classification Search
CPC combination set(s) only.
See application file for complete search history.

(56) References Cited

U.S. PATENT DOCUMENTS

| | | | |
|---|---|---|---|
| 9,649,205 B2 | 5/2017 | Dees, Jr. | |
| 9,826,982 B2 | 11/2017 | Fox et al. | |
| 10,299,801 B2 | 5/2019 | Grant et al. | |
| 11,026,700 B2 * | 6/2021 | Shah | A61F 2/461 |

OTHER PUBLICATIONS

Insall JN, Binazzi R, Soudry M, Mestriner LA. Total knee arthroplasty. Clin Orthop Relat Res, 1985, 192: 13-22. [PubMed] [Google Scholar].
Laskin RS. Alignment of total knee components. Orthopedics, 1984, 7: 62-72. [PubMed] [Google Scholar].
Xiaoyong Chen, Huayi Wang, Yuanzhen Cai, Sagittal component alignment is less reliable than coronal component alignment in a Chinese population undergoing navigated TKA. Journal of Orthopaedic Surgery and Research vol. 9, Article No. 51 (2014).

(Continued)

*Primary Examiner* — Sameh R Boles
(74) *Attorney, Agent, or Firm* — Kilpatrick Townsend & Stockton LLP

(57) ABSTRACT

A medical device to facilitate a distal femoral cut of a femur of a patient is described herein. Such medical devices can include a base having a planar surface along a first plane between a distal end and a proximal end of the base. The medical device also includes one or more projections extending from the distal end of the base. The medical device also includes a cutting guide used to guide cutting of the distal femoral cut and a mounting mechanism that is used to releasably couple the cutting guide to the proximal end of the base. The base, the one or more projections, and the cutting guide are configured to engage various surfaces femoral condyles of the femur when the medical device is placed on a knee joint without requiring insertion of an intermedullary femoral rod into the femoral canal of the knee.

27 Claims, 9 Drawing Sheets

(56) References Cited

OTHER PUBLICATIONS

Ming-Chou Ku, Wei-Jen Chen, Chien-Sheng Lo, Chang-Han Chuang, Zih-Pin Ho, Femoral Component Alignment with a New Extramedullary Femoral Cutting Guide Technique, Indian J Orthop. Mar.-Apr. 2019; 53(2): 276-281doi:10.4103/ortho.IJOrtho_119_17.

Gianluca Castellarin, a novel surgical technique to perform total knee arthroplasty in patients with inaccessible femoral medullary canal, Journal of Orthopaedics; vol. 19, May-Jun. 2020, pp. 102-105.

\* cited by examiner

DISTAL FEMORAL CUTTING BLOCK INSTRUMENT

CROSS REFERENCES TO RELATED APPLICATIONS

This application is a continuation application of U.S. patent application Ser. No. 17/956,468, filed Sep. 29, 2022, entitled "Distal Femoral Cutting Block Instrument," the disclosure of which this application is incorporated by reference herein in its entirety.

BACKGROUND OF THE INVENTION

Total knee arthroplasty (TKA) is a surgical procedure for eradicating advanced knee pain and restoring knee function, thereby improving the quality of life of patients. Limb alignment, protheses selection, precise surgical techniques, and perioperative management are critical to successful surgical procedures.

There are two main methodologies in total knee replacement procedures including mechanical alignment and kinematic alignment. Mechanical alignment creates a neutral hip-knee-ankle (HKA) axis. Kinematic alignment attempts to maintain the natural kinematic axis and ligament balance of the individual knee. Approaches to each of these methodologies include inserting an intermedullary femoral rod in the femoral canal of the knee to couple cutting blocks and align the instruments associated therewith. The intermedullary femoral rod is also used to align the prosthesis in its final position within the coronal and sagittal planes for achieving the optimal functional outcomes and durability of the prosthesis.

Improper positioning of the entry point of the intermedullary rod can significantly affect the position of the femoral component and ultimately, the limb alignment. Individual anatomical variations, e.g., a wide or narrow canal, excessive femoral bowing, etc., coupled with the ever present potential for human error by the surgeon, may result in alignment errors.

An additional risk associated with the insertion of an intermedullary rod is that the rod, and the insertion thereof, damages the cancellous bone and intermedullary vessels which can ultimately lead to fat embolisms and/or postoperative blood loss.

Despite the limitations discussed above, intermedullary alignment instrumentation using intermedullary rod insertion into the femoral canal remains the technique of choice for TKA surgical procedures.

Two alternative approaches have been developed to avoid the hazardous process of intramedullary rod insertion into the femoral canal. Extramedullary rod techniques are imprecise approaches which require that the whole limb be in the surgical field and expose the patient and the surgeon to x-rays to find the femoral canal. A long rod is used at the anterior cortex of the femur. These methods are inaccurate and require additional exposure in the surgical field to soft tissue damage. This approach is limited to use in exceptional cases such as where the patient has relatively significant femoral bowing, femoral mal-unions, obliteration of the canal by orthopedic devices, etc. In at least one extramedullary technique, the tibia is cut first, and the distal femoral cut is controlled by the long extramedullary rods which again lead to imprecise positioning and unfavorable results.

The other alternative approach to intermedullary rods uses technology assisted surgery (e.g., computed navigation, robotic surgery, etc.). The foregoing approach has its own disadvantages including higher cost, longer operation time, longer learning curve for surgeons, etc. Furthermore, proper sagittal positioning of the femoral components using computer navigation can be imprecise. Thus, there is a need for improved approaches that overcome the deficiencies of the above noted conventional approaches.

SUMMARY OF THE INVENTION

Many embodiments provide a novel distal femoral cutting device and method for providing precise placement of the femoral component. The device may be used with the kinematic methodology of TKA surgical procedures. The device may be used with the mechanical methodology of TKA surgical procedures. The device uses intra-articular landmarks available in the surgical field. For example, the condyles of the femur are used as reference surfaces to cut the distal femur perpendicularly to the posterior cortex of the femoral shaft.

DETAILED DESCRIPTION OF THE SPECIFIC EMBODIMENTS

Figure 1:
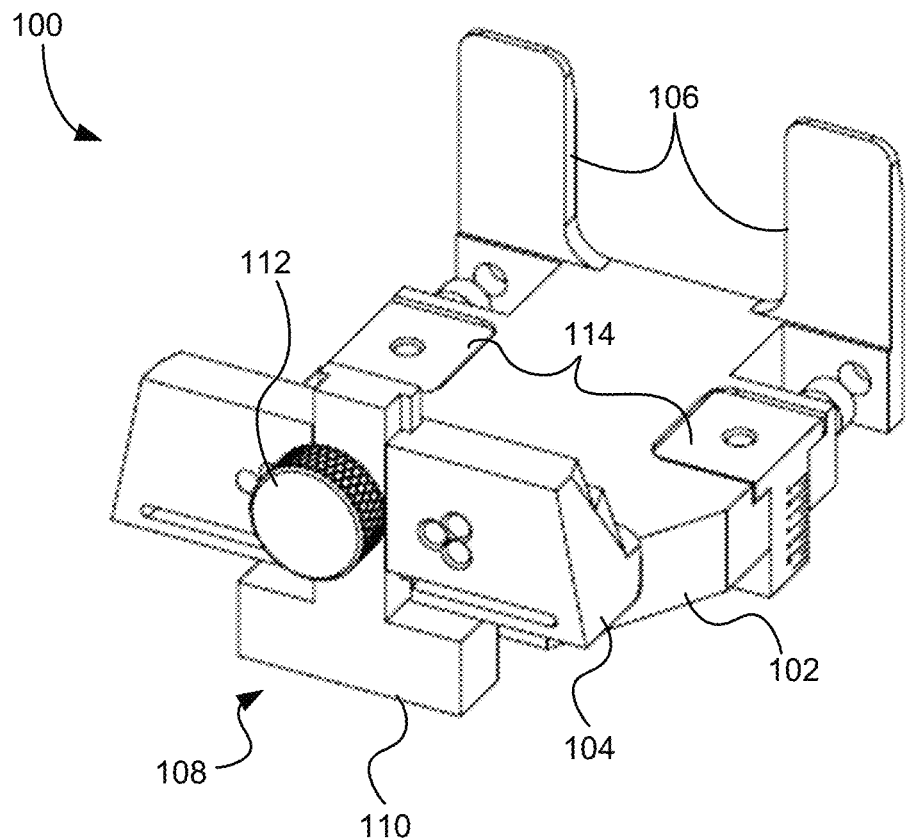
FIG. 1 is perspective drawing of an exemplary distal femoral cutting device, in accordance with one aspect of the present disclosure.

The accompanying drawings, which are incorporated herein and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and can or cannot represent actual or preferred values or dimensions.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed embodiment(s). However, it will be apparent to those skilled in the art that the disclosed embodiment(s) can be practiced without those specific details. In some instances, well-known structures and components can be shown in block diagram form in order to avoid obscuring the concepts of the disclosed subject matter. In the drawings, like reference numerals represent like parts throughout the several views.

The present invention relates generally to a distal femoral cutting device and method for providing precise placement of the femoral component. The device is particularly useful in total knee arthroplasty (TKA) surgical procedures. For example, the medical device as described herein may be used to facilitate a distal femoral cut of a femur of a patient by establishing reference planes to perform the distal femoral cut. The device described herein relies on intra-articular landmarks which are readily available in the standard surgical field for TKA surgical procedures. The femoral condyles are used as reference surfaces to cut the distal femur perpendicular to the posterior cortex of the femoral shaft. Using the condylar surfaces as the landmarks for cutting the distal femur has not previously been explored in the knee arthroplasty field.

Although there is not consensus on the optimal sagittal positioning of the femoral component (e.g., the prosthetic implant which replaces the end of the femur), the majority of the scientific and medical community agree on having a gamma angle in the range of about 0 to about 3 degrees of flexion. According to at least some embodiments described herein, the sagittal positioning of the femoral component is less than 2 degrees of flexion.

FIG. 1 is a medical device 100 to facilitate a distal femoral cut of a femur of a patient. The medical device 100 may include more or less components than those shown here and may include any combination of components described herein. Various components of the medical device 100 described in the present disclosure comprise steel used for medical surgical instruments known in the art.

The medical device 100 includes a base 102 and a cutting guide 104. One or more projections 106 extend from the base 102. The medical device 100 also includes a mounting mechanism 108 that is configured to releasably couple the cutting guide 104 to the base 102.

In at least some aspects, the mounting mechanism 108 includes an adjustment guide 110 for adjusting a position of the cutting guide 104 from the base 102. The adjustment guide 110 preferably includes a ruler in millimeter increments for adjusting the position of the cutting guide 104 from the base 102 and/or for adjusting the thickness of the distal femoral cut. The mounting mechanism 108 may also include a screw tight fastener 112 and one or more rods or bars (shown in FIG. 4). In some embodiments, the fastener 112 is not screw tight and uses another mechanism known in the art to secure the various components of the medical device 100 together. The combination of the adjustment guide 110, the screw tight fastener 112, and the one or more rods releasably couple the cutting guide 104 to the base 102. For example, unscrewing the screw tight fastener 112 releases the cutting guide 104 from the base 102 such that the cutting guide 104 is moveable along the length of the rods of the mounting mechanism 108. The cutting guide 104 may be further removed from the one or more rods and the one or more rods may be removed from the base 102 to complete the decoupling of the cutting guide 104 to the base 102. In a preferred embodiment, the cutting guide 104 may be decoupled from the base 102 by unscrewing the screw tight fastener 112, thereby loosening the remaining components of the medical device 100 for removal from the knee.

In various aspects, the medical device 100 includes at least two spacers 114 along the base 102 for adjusting a cut thickness difference between the femoral condyles and/or a fit of the medical device 100 on the femoral condyles. For example, each spacer may include a ruler in one millimeter increments for adjusting the thickness of the distal femoral cut for each of the medial condyle and the lateral condyle. A different cut thickness may be desired in some approaches for the medial condyle and the lateral condyle. In other embodiments, the spacers 114 may be used to adjust the fit of the medical device 100 on the femoral condyles. In preferred aspects, the medical device 100 includes two spacers, one on each lateral side of the base. Each spacer may be held in place by a pin, a screw, a magnet, a fastener, etc., (not shown) which secures the spacer in the adjusted position.

According to preferred aspects, the base 102, the one or more projections 106, and the cutting guide 104 are configured to engage femoral condyles of the femur when the medical device 100 is placed on a knee joint. For example, the one or more projections 106 align with the posterior surfaces of the medial and lateral condyles when the tibia is in 90 degrees of flexion and the base 102 engages the distal surfaces of the medial and lateral condyles using the spacers 114.

Figure 2:
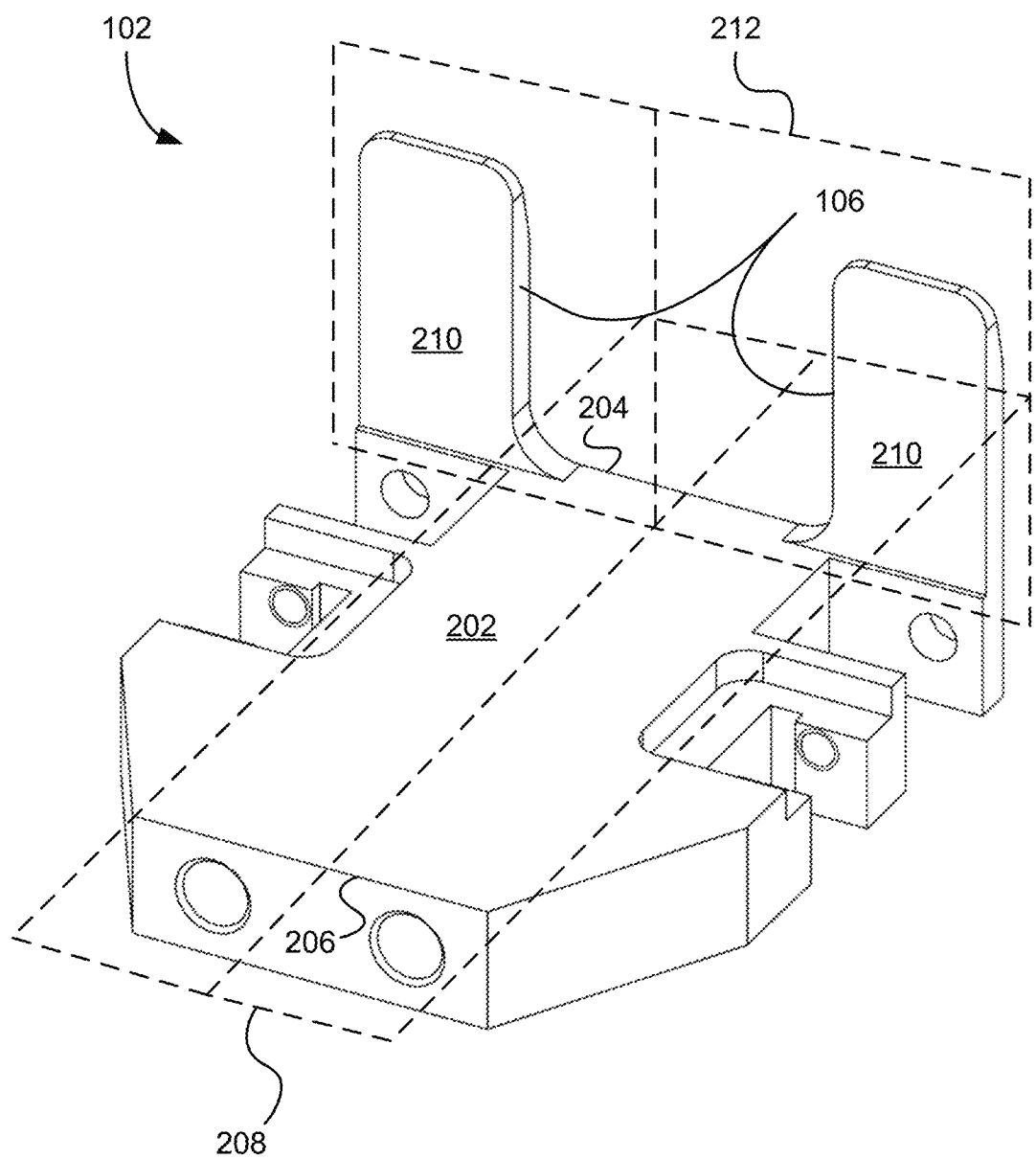
FIG. 2 is a perspective drawing of an exemplary base, in accordance with one aspect of the present disclosure.

FIG. 2 is a base 102 of medical device 100. The base 102 may include more or less components than those shown here and may include any combination of components described herein.

The base 102 includes a planar surface 202 extending from a distal end 204 to a proximal end 206 of the base 102. The planar surface 202 is along a first plane 208. The one or more projections 106 extend from the distal end 204 of the base 102 in preferred configurations. The one or more projections 106 may be the same length or a different length. In some aspects, the one or more projections 106 may be different lengths for extreme body sizes. For example, a typical length (e.g., suitable for 90% of patients) for the one or more projections may be 10 millimeters. The one or more projections 106 may be about 5 to about 7 millimeters in length for short statures and less than or equal to 15 millimeters for larger statures.

The planar surface 202 of the base 102 is configured to engage along distal facing surfaces of femoral condyles of a patient when the medical device 100 is placed on the knee joint. For example, at least a portion of the planar surface 202 of the base 102 is in contact with the distal surfaces of the femoral condyles when the medical device 100 is placed on the knee joint.

In various aspects, the one or more projections 106 have planar surfaces 210. The planar surfaces 210 are typically along a second plane 212 which is perpendicular to the first plane 208. The planar surfaces 210 face the base 102, particularly the distal end 204 of the base 102. The one or more projections 106 are configured to engage along posterior facing surfaces of the femoral condyles when the medical device 100 is placed on the knee joint. For example, at least a portion of the planar surfaces 210 of the one or more projections 106 are in contact with the posterior surfaces of the femoral condyles when the medical device 100 is placed on the knee joint.

Figure 3:
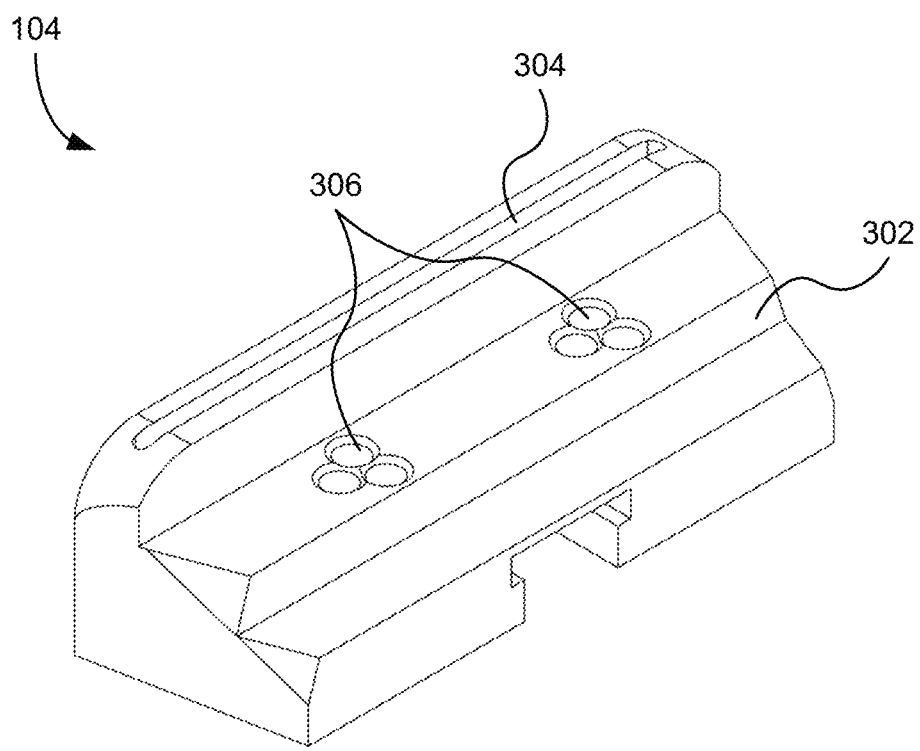
FIG. 3 is a perspective drawing of an exemplary cutting guide, in accordance with one aspect of the present disclosure.

FIG. 3 is a cutting guide 104 of medical device 100. The cutting guide 104 may include more or less components than those shown here and may include any combination of components described herein.

The cutting guide 104 is configured to guide cutting of the distal femoral cut. The cutting guide 104 includes a stepped face surface 302. The stepped face surface 302 preferably faces the base 102 (not shown) when releasably coupled to the base 102 via the mounting mechanism 108 (not shown). The stepped face surface 302 is configured to engage along anterior facing surfaces of the femoral condyles when the medical device 100 is placed on the knee. For example, at least a portion of the stepped face surface 302 is in contact with the anterior surfaces of the femoral condyles when the medical device 100 is placed on the knee. The stepped surface enables the medical device 100 to grip to the femoral condyles along the rounded surfaces of the femoral condyles.

The cutting guide 104 includes a slot 304 extending therethrough. The slot 304 preferably extends along a plane parallel to the first plane 208 of the planar surface 202 of the base 102 (not shown) when the cutting guide 104 is releasably coupled to the base 102 via the mounting mechanism 108. The slot 304 enables a cutting mechanism (e.g., a bone saw, a blade, a rotary drill, etc.) to extend therethrough during operation for performing the distal femoral cut. In preferred aspects, the width and/or the height of the slot 304 contain movement of the cutting mechanism therethrough consistently parallel to the first plane 208 of the base 102. For example, the width of the slot 304 may be thin enough and the height of the slot 304 may be tall enough such that the cutting mechanism easily slides through and performs the cut, but the cutting mechanism does not wiggle back and forth (e.g., perpendicularly to the first plane 208) during operation.

The cutting guide 104 includes at least two openings 306 for passage of at least two fastening members into the femur for securing the cutting guide 104 to the anterior facing surfaces of the femoral condyles when the medical device 100 is placed on a knee joint. In some approaches, the cutting guide 104 includes at least two openings 306, one at each lateral end of the cutting guide 104 (e.g., one above the medial femoral condyle and one above the lateral femoral condyle when the cutting guide 104 is placed on the knee). In preferred approaches, the cutting guide 104 includes six openings 306 where a group of three offset openings 306 are located at each lateral end of the cutting guide 104, as shown. For example, in the grouping of openings 306, each opening 306 may be offset from the other by one or more millimeters for enabling greater flexibility in placement of the fastening members into the femur. In one exemplary aspect, the groupings of opening 306 are located such that an outermost pair of openings are spaced 8 millimeters apart, a middle pair of openings are spaced 6.5 millimeters apart, and an innermost pair of openings are spaced 6 millimeters apart to provide a physician with the ability to select a precise location to drill at least two holes for insertion of fastening members.

Figure 4:
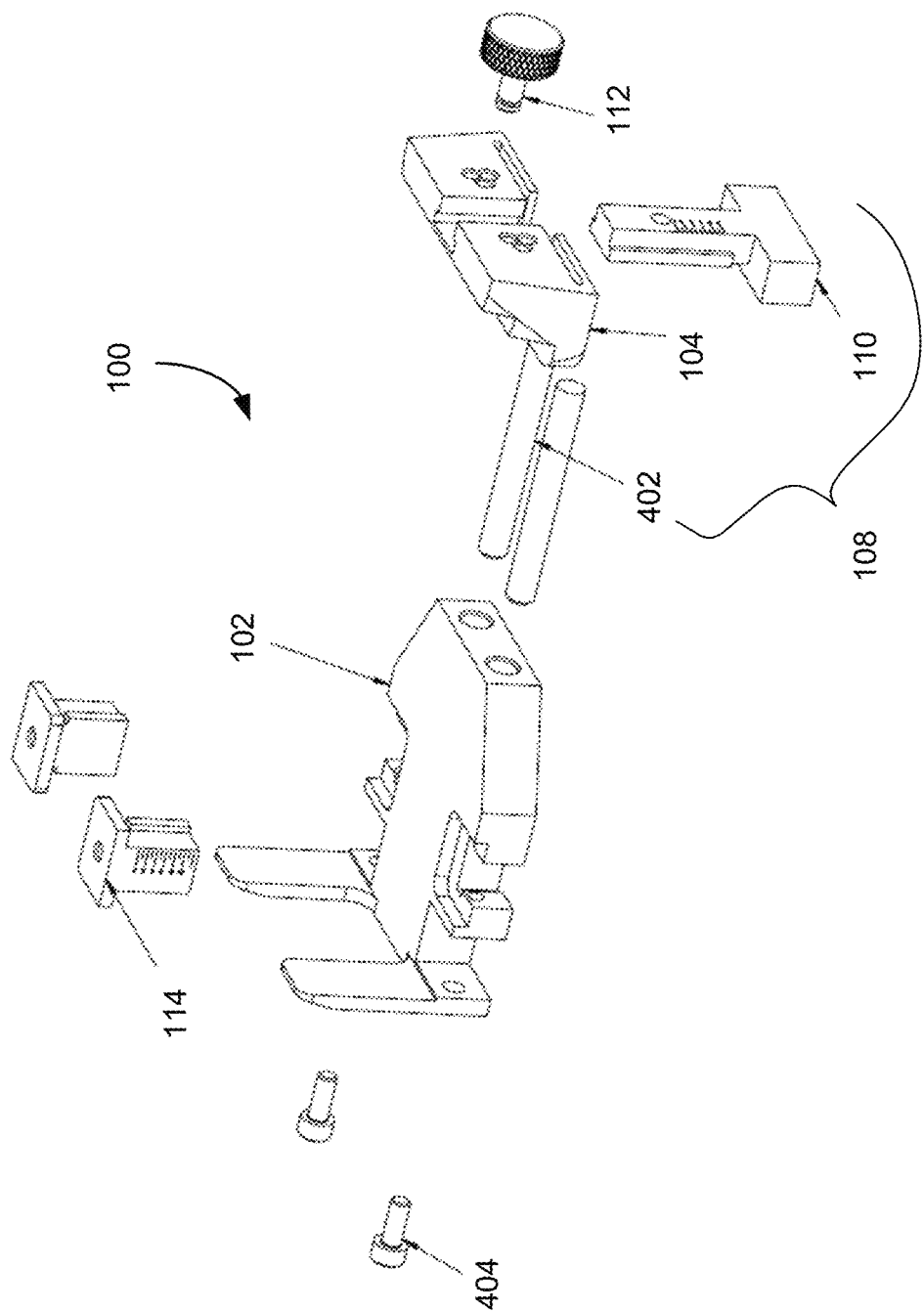
FIG. 4 is an exploded perspective drawing of an exemplary distal femoral cutting device in accordance with one aspect of the present disclosure.

FIG. 4 is an exploded view of the medical device 100 including the base 102, the cutting guide 104, and the mounting mechanism 108 including the adjustment guide 110, the screw tight fastener 112 and the rods 402. The rods 402 lay in slots of the base 102 (not shown) in a secure position. The rods 402 may be coupled to the adjustment guide 110. In preferred aspects, the mounting mechanism 108 includes at least two rods 402 (as shown) with screws 404 which hold the spacers 114 in place at the selected adjustment positions. While two rods are shown, it is appreciated that various other means could be used, such as one or more elongated bars, plates, or any suitable component or mechanism.

FIGS. 5-8 illustrate the exemplary distal femoral cutting device 100 during operation, in accordance with one aspect of the present disclosure.

Figure 5:
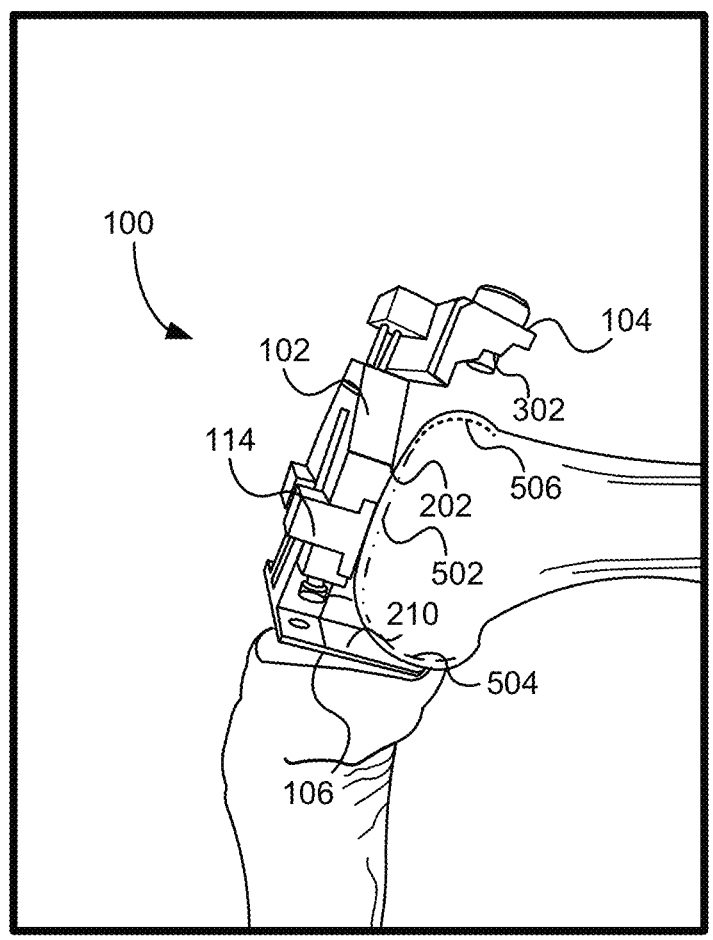
FIGS. 5-8 illustrate the exemplary distal femoral cutting device during operation, in accordance with one aspect of the present disclosure.
Figure 6:
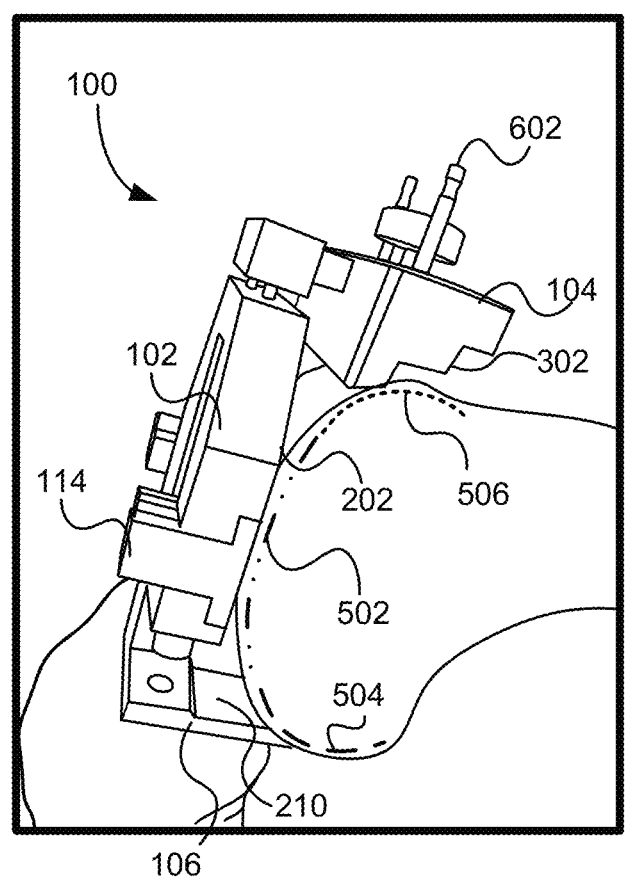

FIG. 5 shows the medical device 100 in relation to its final position placed on the knee (as shown in FIG. 6). As shown, the planar surface 202 of the base 102 is engaged with the distal facing surfaces 502 of the femoral condyles when the knee is bent. The position of a bent knee may be defined as when the knee and tibia is in 90 degree flexion (e.g., the orientation of the cutting guide is perpendicular to the posterior condyle and/or the femoral canal). The spacers 114 may be used to make further adjustments, e.g., to increase the engagement of the planar surface of the base 102 with the distal facing surfaces 502 of the femoral condyles and/or to stabilize the medical device 100 along the knee joint. The planar surfaces 210 of the one or more projections 106 are engaged with the posterior facing surfaces 504 of the femoral condyles when the knee is bent. The stepped face surface 302 of the cutting guide 104 is generally parallel to the anterior facing surfaces 506 of the femoral condyles when the knee joint is bent and the stepped face surface 302 is configured to engage with the anterior facing surfaces 506 of the femoral condyles when the medical device 100 is in its final position placed on the knee.

FIG. 6 shows the medical device 100 in its final position placed on the knee. As shown, the planar surface 202 of the base 102 is engaged with the distal facing surfaces 502 of the femoral condyles when the knee is bent. The spacers 114 may be used to make further adjustments, e.g., to increase the engagement of the planar surface of the base 102 with the distal facing surfaces 502 of the femoral condyles and/or to stabilize the medical device 100 along the knee joint. The planar surfaces 210 of the one or more projections 106 are engaged with the posterior facing surfaces 504 of the femoral condyles when the knee is bent. The stepped face surface 302 of the cutting guide 104 is engaged with the anterior facing surfaces 506 of the femoral condyles when the knee joint is bent.

At least two holes may be drilled through the openings 306 (not shown) of the cutting guide 104 into the anterior facing surfaces 506 of the femoral condyles (e.g., into the femur) of the patient and at least two fastening members 602 (e.g., nails) are inserted into the openings of the cutting guide 104 and through to the drilled holes for securing the cutting guide 104 and the releasably coupled base 102 to the femoral condyles.

Figure 7:
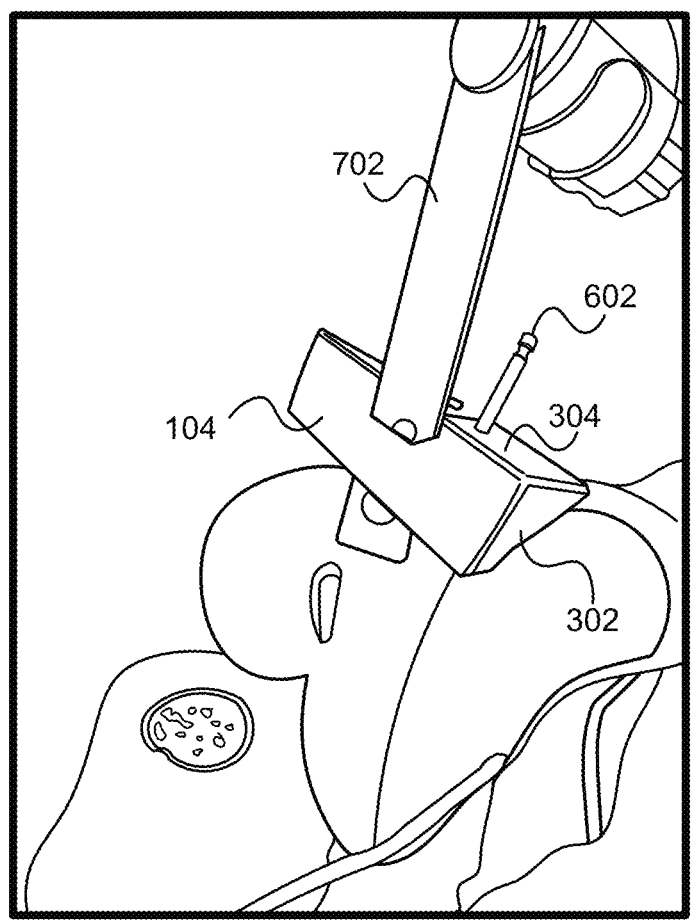

FIG. 7 shows the cutting guide 104 secured to the anterior surfaces of the femoral condyles via the at least two fastening members 602. The base 102 is decoupled from the cutting guide 104 using the mounting mechanism 108, leaving only the cutting guide 104 secured to the anterior surface of the femoral condyles by the two fasteners 602. The stepped face surface 302 of the cutting guide 104 is engaged with the anterior facing surfaces of the femoral condyles. A blade 702 is inserted through the slot 304 of the cutting guide 104 for performing the distal femoral cut of the femur.

Figure 8:
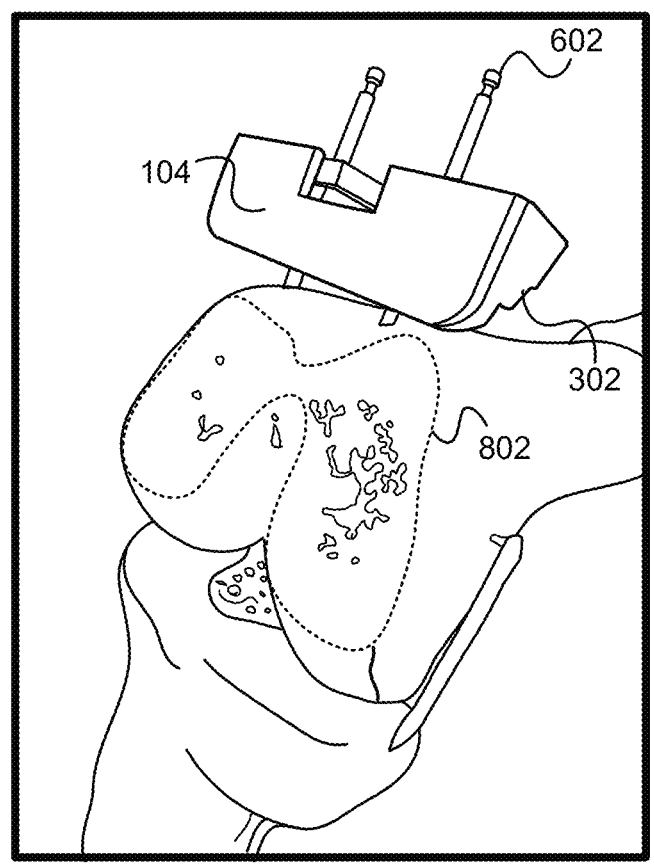

FIG. 8 shows the cutting guide 104 secured to the anterior surfaces of the femoral condyles via the at least two fastening members 602 following the cutting of the distal femoral cut 802. The stepped face surface 302 of the cutting guide 104 may be removed from the anterior facing surfaces of the femoral condyles by sliding the cutting guide 104 along the fastening members 602 or the fastening members 602 may be removed prior to or substantially simultaneously with the cutting guide 104.

Figure 9:
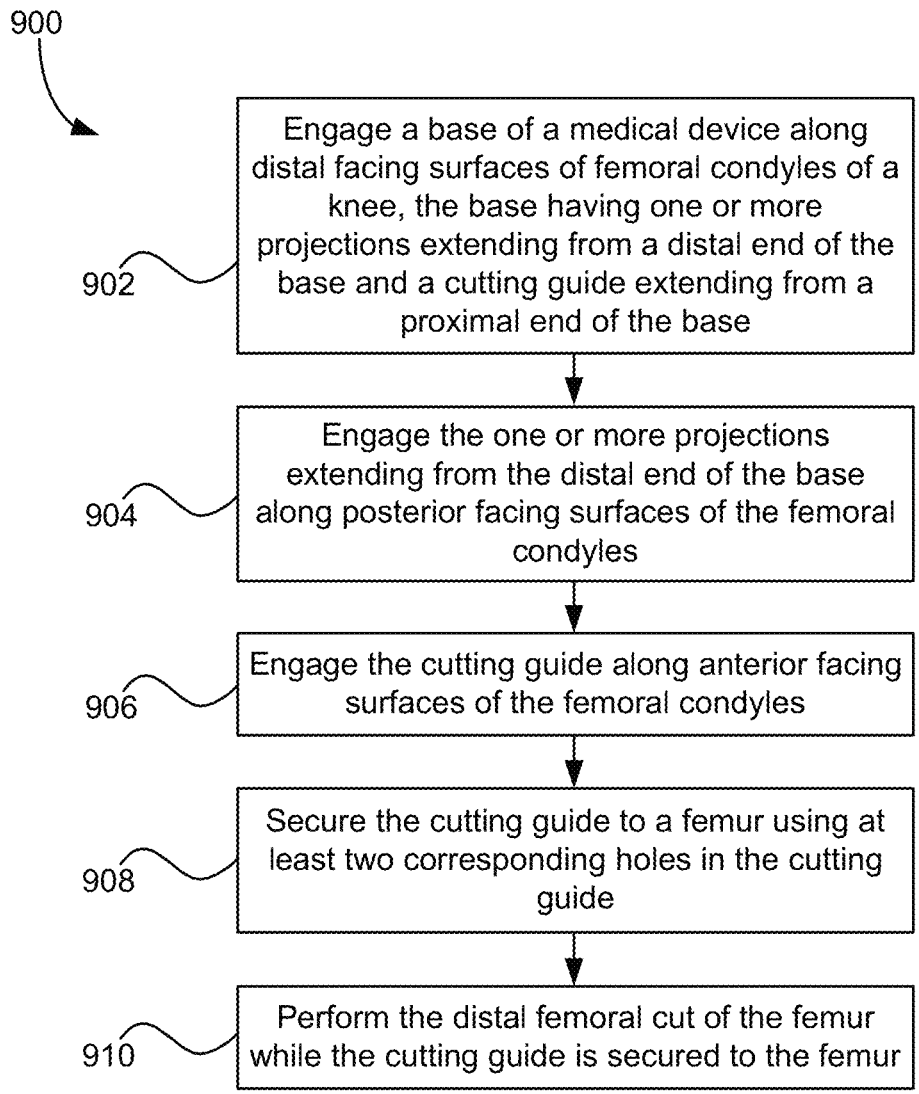
FIG. 9 is a flowchart of a method, in accordance with one aspect of the present disclosure.

FIG. 9 is a flowchart of a method 900 for establishing references planes to perform a distal femoral cut, in accordance with one aspect of the present disclosure. The method may have more or less operations than those listed herein.

Method 900 includes operation 902. Operation 902 includes engaging a base of a medical device along distal facing surfaces of femoral condyles of a knee, the base having one or more projections extending from a distal end of the base and a cutting guide extending from a proximal end of the base. The base preferably includes a planar surface along a first plane between the distal end and the proximal end of the base. The planar surface of the base is typically configured to engage along the distal facing surfaces of the femoral condyles.

In at least some approaches, operation 902 may include adjusting at least two spacers along the base for maintaining the different thicknesses of the cut in the medial and lateral condyles. For example, the at least two spacers may be used in complex cases where the femoral condyles are uneven or otherwise warped. In one exemplary application, one of the femoral condyles may be 2 millimeters less than (or greater than) the other of the femoral condyles. The spacers may be used to accommodate this difference when positioning the base and engaging the base with the distal surfaces of the femoral condyles.

The two spacers enable a secure engagement between the base of the medical device and the distal facing surfaces of the femoral condyles. The two spacers may also be used to adjust the thickness of the distal femoral cut to be performed. For example, the at least two spacers may be used to adjust the height of the base in relation to the distal surfaces of the femoral condyles.

Operation 904 includes engaging the one or more projections extending from the distal end of the base along posterior facing surfaces of the femoral condyles. The one or more projections preferably include planar surfaces which face the base. The planar surfaces of the one or more projections are along a second plane which is perpendicular to the first plane (e.g., of the planar surface of the base). The planar surfaces of the one or more projections along the second plane are configured to engage along the posterior facing surfaces of the femoral condyles.

Operation 906 includes engaging the cutting guide along anterior facing surfaces of the femoral condyles. The cutting guide preferably comprises a stepped surface. The stepped surface of the cutting guide is configured to engage along the anterior facing surfaces of the femoral condyles. In other approaches, the cutting guide has a textured surface other than a stepped face for engaging (e.g., gripping) the anterior facing surfaces of the femoral condyles. In one example, the cutting guide may have a patterned surface and/or gritted surface for engaging the anterior facing surfaces of the femoral condyles.

In various approaches, engaging a base of a medical device along distal facing surfaces of femoral condyles of a knee and engaging the cutting guide along anterior facing surfaces of the femoral condyles occurs substantially simultaneously. For example, the base may be releasably coupled to the cutting guide via a mounting mechanism prior to placement on the knee such that both the base and the cutting guide engage with their respective surfaces during placement at substantially the same time. Similarly, the one or more projections extending from the distal end of the base may be engaged along posterior facing surfaces of the femoral condyles at substantially the same time as the base and the cutting guide. In other approaches, the base is placed on the knee first (e.g., such that the base engages along the distal facing surfaces of the femoral condyles and the one or more projections extending from the distal end of the base engage along the posterior facing surfaces of the femoral condyles at substantially the same time), and then the cutting guide is releasably coupled to the base via the mounting mechanism. The cutting guide then engages along anterior facing surfaces of the femoral condyles, in the foregoing approach.

Operation 908 includes securing the cutting guide to a femur using at least two corresponding holes in the cutting guide. In various approaches, operation 908 may include drilling into the femoral condyles through the at least two holes in the cutting guide. The at least two holes are located on an anterior facing surface of the cutting guide and the openings of the at least two holes are substantially parallel to the anterior surfaces of the femoral condyles. The cutting guide may be secured to the anterior facing surfaces of the femoral condyles using at least two fastening members inserted through the at least two holes of the cutting guide and the at least two drilled holes in the femoral condyles. For example, the fastening members may include rods, nails, screws, etc., which temporarily secure the cutting guide to the femoral condyles. The fastening members are preferably relatively easy to remove after the distal femoral cut is performed. For example, nails may be removed by a physician using pliers resulting in relatively minor trauma to the femur.

Method 900 may include decoupling the cutting guide from the base prior to performing the distal femoral cut. The decoupling may be performed using the mounting mechanism. In various approaches, the mounting mechanism includes a screw tight fastener and one or more rods or bars. The mounting mechanism further includes the adjustment guide for adjusting the position of the base relative to the cutting guide and/or to adjust a thickness of the distal femoral cut by adjusting the space between the base and the distal surfaces of the femoral condyles. Accordingly, decoupling the cutting guide from the base may include untightening the screw tight fastener and removing the base, the adjustment guide, and/or the rods from the cutting guide. For example, all the components of the medical device are removed from the knee joint except the cutting guide which remains secured to the anterior surfaces of the femoral condyles via the at least two fastening members.

Operation 910 includes performing the distal femoral cut of the femur while the cutting guide is secured to the femur. Performing the distal femoral cut of the femur comprises inserting a blade or other cutting mechanism known in the art through a slot in the cutting guide and cutting across a distal portion of the femur. The distal femoral cut leaves a substantially flat (e.g., planar) surface in the distal portion of the femoral condyles (such as the distal femoral cut 802 as shown in FIG. 8).

Following performing the distal femoral cut, method 900 may include removing the at least two fastening members and the cutting guide from the knee and applying a means to perform additional cuts of the femoral condyles. For example, after establishing the plane for the distal femoral cut using the medical device described herein, a physician may use techniques and instruments known in the art to complete the TKA surgical procedure, using the plane of the distal femoral cut as a reference point for all other cuts to the femoral condyles. The medical device used in the method described above is compatible with any prosthesis known in the art.

According to various aspects described herein, the distal femoral cutting device includes at least four contact points for determining a distal reference plane. For example, the base engages with each of the distal surfaces of the femoral condyles, and each of at least two projections engages with the posterior surfaces of the femoral condyles. When the tibia and the femur are in 90 degrees of flexion the medical device lies on at least the distal and posterior surfaces of the femur, the physician is able to determine a position which is substantially perpendicular to the posterior condylar surface for performing the distal femoral cut. When the tibia is in 90 degree of flexion the structure of the medical device described herein guides the surgeon to cut the distal femur perpendicularly to the posterior cortex of the femur.

The medical device as described herein aligns the femoral component in the correct sagittal plane. In other approaches, the medical device may be used to align the femoral components in the correct coronal plane. A correct sagittal plane may be defined as the plane perpendicular to posterior cortex of femoral shaft as seen from a lateral view of the femur and knee. A correct coronal plane may be defined by the orientation of the cut or femoral component relative to the femoral shaft from a front view of the knee.

Importantly, the medical device described throughout the present disclosure does not require the use of any intermedullary rods and/or penetration of the femoral canal. Furthermore, the medical device and/or methods described herein do not rely on landmarks outside of the knee joint (e.g., such as conventionally available extramedullary techniques).

At least some aspects of the medical device and/or methods described herein may be used with kinematic and/or mechanical-based philosophies which used in knee arthroplasty. Kinematic and mechanical philosophies have different thoughts about best orientation for components to achieve best outcomes and survival. Those who practice the mechanical philosophy believe the components should be perpendicular to femoral and tibial shaft regardless of the native knee anatomy. In contrast, those who practice the kinematic philosophy believe that the orientation of components should be the same as the native knee anatomy. The spacers provided in the medical device described herein are able to accommodate both of these philosophies.

In at least some kinematic methods, the difference in the distal femoral cut of the medial condyle and the distal condyle is 2 millimeters. Accordingly, in some approaches, the medical device described herein may omit at least one of the spacers to maintain the difference in cut by 2 millimeters. In other approaches, the medical device may be 2 millimeters thicker on one side of the base to account for the difference.

In at least some mechanical methods, the difference between medial and lateral cut in every patient is individualized and is determined pre-operatively by x-rays. The cuts may be adjusted during operation adjusted using the spacers on each side of the medical device described herein.

What is claimed is:

1. A medical device to facilitate a distal femoral cut of a femur of a patient, the medical device comprising: a base comprising a planar surface extending along a first plane between a distal end and a proximal end of the base; one or more projections extending from the distal end of the base; a cutting guide configured to guide cutting of the distal femoral cut; and a mounting mechanism releasably coupling the cutting guide with the base along the proximal end of the base; wherein the base, the one or more projections, and the cutting guide are configured to engage femoral condyles of the femur when the medical device is placed on a knee joint, wherein the cutting guide comprises a stepped surface facing the base, the stepped surface configured to engage along anterior facing surfaces of the femoral condyles when the medical device is placed on the knee joint.

2. The medical device of claim 1, wherein the planar surface of the base is configured to engage along distal facing surfaces of the femoral condyles when the medical device is placed on the knee joint.

3. The medical device of claim 1, wherein the one or more projections have planar surfaces which face the base, the planar surfaces being along a second plane which is perpendicular to the first plane.

4. The medical device of claim 1, wherein the one or more projections comprise at least two planar projections that are configured to engage along posterior facing surfaces of the femoral condyles when the medical device is placed on the knee joint.

5. The medical device of claim 1, wherein the cutting guide comprises a slot extending therethrough for performing the distal femoral cut.

6. The medical device of claim 5, wherein the slot extends along a plane parallel to the planar surface of the base.

7. The medical device of claim 1, wherein the mounting mechanism comprises a screw tight fastener and one or more rods or bars.

8. The medical device of claim 7, wherein the mounting mechanism comprises at least two rods that extend into the base.

9. The medical device of claim 1, wherein the mounting mechanism comprises an adjustment guide configured to adjust a position of the cutting guide from the base.

10. The medical device of claim 1, wherein the cutting guide comprises at least two openings for passage of at least two fastening members into the femur for securing the cutting guide to the anterior facing surfaces of the femoral condyles when the device is placed on the knee joint.

11. The medical device of claim 1, further comprising at least two spacers along the base for adjusting a thickness of the distal femoral cut in each femoral condyle and/or a fit of the device on the femoral condyles.

12. The medical device of claim 11, wherein the at least two spacers comprise one spacer on each lateral side of the base.

13. A medical device to facilitate a distal femoral cut of a femur of a patient,
the medical device comprising: a base portion comprising a surface extending along a first plane between a distal end and a proximal end; one or more projecting portions having at least one surface extending in a second plane perpendicular from the first plane, the one or more projecting portions protruding from the base portion along or near the distal end of the base portion; and a cutting guide coupled to the base portion, the cutting guide configured to guide cutting of the distal femoral cut; wherein the base portion, the one or more projecting portions, and the cutting guide are configured to engage femoral condyles of the femur when the medical device is placed on a knee joint of the patient, wherein the cutting guide comprises a textured surface facing the base portion, the textured surface configured to engage along anterior facing surfaces of the femoral condyles when the medical device is placed on the knee.

14. The medical device of claim 13, wherein the surface of the base portion is configured to engage along distal facing surfaces of the femoral condyles when the medical device is placed on the knee joint.

15. A medical device to facilitate a distal femoral cut of a femur of a patient,
the medical device comprising: a base comprising a planar surface between a distal end and a proximal end; and a cutting guide configured to guide cutting of the distal femoral cut; and wherein the base and the cutting guide are configured to engage femoral condyles of the femur when the medical device is placed on a knee joint to facilitate cutting of the distal femoral cut without requiring insertion of an intermedullary femoral rod into the femoral canal of the knee, wherein the cutting guide has a textured surface for engaging anterior facing surfaces of the femoral condyles when the medical device is placed on the knee joint.

16. The medical device of claim 15, wherein the base and the cutting guide are releasably coupled via a mounting mechanism.

17. The medical device of claim 16, wherein the mounting mechanism comprises a screw tight fastener and one or more rods or bars.

18. The medical device of claim 16, wherein the mounting mechanism comprises an adjustment guide for adjusting a position of the cutting guide relative to the base.

19. The medical device of claim 18, wherein the adjustment guide includes a ruler in millimeter increments for adjusting the position of the cutting guide from the base.

20. The medical device of claim 17, wherein the cutting guide is moveable along the length of the rods of the mounting mechanism.

21. The medical device of claim 15, comprising at least two spacers along the base for adjusting a thickness of the distal femoral cut in each femoral condyle and/or a fit of the device on the femoral condyles.

22. The medical device of claim 21, wherein each of the at least two spacers includes a ruler in millimeter increments for adjusting the thickness of the distal femoral cut for each of the femoral condyles.

23. A medical device to facilitate a distal femoral cut of a femur of a patient, the medical device comprising:
   a base comprising a planar surface extending along a first plane between a distal end and a proximal end of the base, wherein the planar surface of the base is configured to engage with distal facing surfaces of femoral condyles when the medical device is placed on a knee joint;
   one or more projections extending from the distal end of the base, wherein the one or more projections have one or more planar surfaces that are configured to engage along posterior facing surfaces of the femoral condyles when the medical device is placed on the knee joint;
   a cutting guide configured to guide cutting of the distal femoral cut, wherein the cutting guide comprises a stepped surface facing the base, the stepped surface configured to engage along anterior facing surfaces of the femoral condyles when the medical device is placed on the knee; and
   a mounting mechanism that is configured to releasably couple the cutting guide along the proximal end of the base.

24. The medical device of claim 23, wherein the one or more projections have one or more planar surfaces which face the base, the planar surfaces being along a second plane which is perpendicular to the first plane.

25. The medical device of claim 23, wherein a combination of the base, the one or more projections, and the cutting guide provide at least four contact points with the femoral condyles thereby providing stable alignment for performing the distal femoral cut of the femur of the patient.

26. The medical device of claim 23, wherein the one or more projections are different lengths.

27. The medical device of claim 25, wherein the medical device is configured to provide suitable stability and alignment for performing the distal femoral cut without requiring penetration of a femoral canal of the femur of the patient.

* * * * *